United States Patent [19]

Shryne et al.

[11] 4,024,165

[45] May 17, 1977

[54] PROCESS FOR THE EPOXIDATION OF OLEFINS

[75] Inventors: Thomas M. Shryne; Leo Kim, both of Houston, Tex.

[73] Assignee: Shell Oil Company, Houston, Tex.

[22] Filed: June 29, 1976

[21] Appl. No.: 700,994

[52] U.S. Cl. .................................... 260/348.5 L
[51] Int. Cl.$^2$ .................................... C07D 301/12
[58] Field of Search ............................ 260/348.5 L

[56] References Cited

UNITED STATES PATENTS

| | | | |
|---|---|---|---|
| 3,597,459 | 8/1971 | Mimoun et al. | 260/429 |
| 3,778,451 | 12/1973 | Poite | 260/348.5 L |
| 3,953,362 | 4/1976 | Lines et al. | 252/431 N |

FOREIGN PATENTS OR APPLICATIONS 2,082,811  12/1971  France ................ 260/348.5 L

*Primary Examiner*—Norma S. Milestone

[57] ABSTRACT

A process for the epoxidation of olefins in which olefin and hydrogen peroxide are brought into contact in a fluorinated alcoholic solvent in which are dissolved a transition metal compound and a nitrogen-containing organic compound are described.

10 Claims, No Drawings

PROCESS FOR THE EPOXIDATION OF OLEFINS

BACKGROUND OF THE INVENTION

1. Field of the Invention

This invention relates to a process for the epoxidation of olefins by hydrogen peroxide in fluorinated alcohols in the presence of a soluble transition metal compound and a soluble nitrogen-containing organic compound.

2. Description of the Prior Art

It is known that olefins can be epoxidized using hydrogen peroxide in organic solvents in the presence of a transition metal compound and a nitrogen-containing carbon compound. Alcohols have been suggested and used as a solvent for epoxidation but not when hydrogen peroxide was the reactant (U.S. Pat. No. 3,778,451 issued Dec. 11, 1973). The use of an alcohol in which all of the reactants and catalysts are soluble would greatly enhance the production of epoxide when using hydrogen peroxide but hitherto all alcohols employed were subject to oxidation and therefore interfered with the production of epoxide. For example, the epoxidation of propylene to propylene oxide with $H_2O_2$ in isopropyl alcohol is not possible under normal epoxidation conditions.

The present invention is an olefin epoxidation process in an alcoholic organic solvent in which all of the reactants and catalysts are soluble.

The epoxides made by this process may be utilized in the production of certain polymers such as polyoxyethylene and polyoxypropylene or as resin forming monomers such as epichlorohydrin.

SUMMARY OF THE INVENTION

The invention relates to a process for the production of epoxides by contacting an olefin with hydrogen peroxide in a fluorinated alcoholic solvent in the presence of a soluble transition metal compound and a soluble nitrogen-containing carbon compound.

DESCRIPTION OF THE PREFERRED EMBODIMENTS

This invention relates to a process for epoxidizing an olefin in an inert organic solvent in which all of the reactants and catalyst components are soluble.

The invention relates to a process for epoxidizing a variety of ethylenically unsaturated compounds with a soluble catalyst system in a non-oxidizable alcoholic solvent.

The olefins useful in this process are those containing at least one ethylenic saturation. In general, any hydrocarbon olefin having from 2 to about 20 carbons can be oxidized. The aliphatic hydrocarbon mono-olefins include: ethylene, propylene, butene-1, butene-2, isobutene, pentene-1, pentene-2, hexene, isohexene, heptene, 3-methylhexene, octene-1, isooctene, nonene, decene, dodecene, tridecene, pentadecene, octadecene, eicosene, docosene, tricosens, tetracosene, pentacosene, etc. Examples of hydrocarbon diolefins which can also be oxidized include butadiene, pentadiene, hexadiene, octadiene, decadiene, tridecadiene, eicosadiene, tetracosadiene, etc. The alicyclic hydrocarbon olefins can also be oxidized such as cyclopentene, cyclohexene, cycloheptene, methylcyclohexene, isopropylcyclohexene, butylcyclohexene, octylcyclohexene, dodecyclohexene, etc. The preferred olefins are propylene, allyl alcohol and allyl chloride. The most preferred olefin is propylene.

Various of the compounds of the transition metals of molybdenum, tungsten, vanadium, niobium, tantalum, uranium, or rhenium can be utilized as long as they are soluble in the reaction medium, such as, for example, anhydrides, acids, heteropoly acids, organic esters, and complexes like acetylacetonates, etc. The transition metal compound is employed in the reaction mixture in an amount within the range of about 0.001 and about 1 gram-transition metal per liter, preferably about 0.01 to about 0.1.

Excellent results can be obtained by the use of tungsten and molybdenum compounds derived from tungsten or molybdenum anhydrides, such as the hydrates of tungsten and molybdenum anhydride, the molybdic acid of Graham and Murgier, the esters of tungstic and molybdic acid, such as propylene glycol tungstate or molybdate, tungsten and molybdenum complexes, such as that with acetylacetone, heteropoly acids of tungstenum or molybdenum, such as the phosphomolybdic acids, or mixtures of these compounds. The preferred transition metal compound is tungstic acid.

The nitrogen-containing compounds are the amines or amine oxides. These compounds have the formulas $R_3N$, $R_3NO$, ANR and $$\overset{O}{ANR}$$

where R is an alkyl group having 1 to 5 inclusive carbon atoms; a cyclopentyl or cyclohexyl group or a phenyl group and where A is a 4 or 5 carbon saturated chain and A and N form a 5 or 6 membered ring. Preferred amines are trimethylamine, triethylamine, and tripropylamine. Preferred amine oxides are trimethylamine oxide, triethylamine oxide, and tripropylamine oxide.

The fluorinated alcoholic solvents are described by the following formulas:

where $R^1$ is individually a saturated alkyl or fluro alkyl of from 1–6 atoms, a phenyl group, or a fluorine atom and $R^2$ is an alkyl or fluoro alkyl of 2 or 3 carbon atoms which together with the

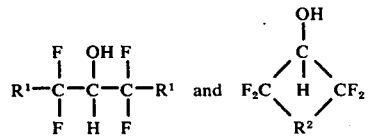

forms a 5 or 6 membered ring. The group $R^1$ is preferably a fluorine atom or per fluoro methyl and the group $R^2$ is preferably per fluoro propylene group ($-CF_2-CF_2-CF_2-$). The preferred solvent is hexafluoro isopropanol

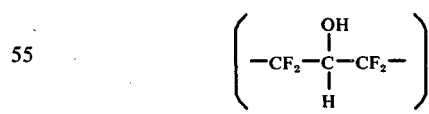

and perfluoromethyl, perfluoroethylcarbinol

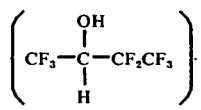

$$\left( \begin{array}{c} \text{OH} \\ | \\ CF_3-C-CF_2CF_3 \\ | \\ H \end{array} \right)$$

These solvents are used inclusive of the presence of substantial impurities such as ketones or acids.

The preferred mode of carrying out the invention is to prepare a solution of hydrogen peroxide in the fluorinated alcohol and add olefin or add olefin and $H_2O_2$ simultaneously to the fluorinated alcohol solution. Preferred concentrations of hydrogen peroxide in the fluoro alcohol are in the range of about 2 to about 25 percent, preferably in the range of about 5 to about 20 percent, and most perferably in the range of about 10 to about 15 percent, based on the total weight or reactants.

The hydrogen peroxide is normally added as an aqueous solution, usually a 50% by weight aqueous solution but care should be taken to see that concentrations are used which maintain the total water content less than 25%, preferably less than 20% and most preferably less than 15% based on the weight of fluoro alcohol and aqueous peroxide including the water produced during the reaction.

Preferred concentrations of transition metal compounds are in the range of about 0.001 to about 1 gram atom/liter fluoro alcohol, and most preferred are about 0.01 to about 0.1 gram atom/liter fluoro alcohol. Preferred concentration of nitrogen-containing carbon compounds are in the range of about 0.01 to about 1 equivalent per liter fluoro alcohol most preferably about 0.1 to about 0.5.

The temperature is kept in the range of about 20° C to about 150° C, preferably about 50° C to about 90° C. The reaction time may vary from about 8 minutes to about 10 hours, preferably from about 0.5 hour to about 2 hours. The reaction pressure can be atmospheric, subatmospheric or supra-atmospheric. Supra-atmospheric pressure is preferred, preferably from about 32 to about 1000 psi, most preferably from about 100 to about 500 psi.

The process may be run in a batch mode or a stepwise batch mode or a continuous mode where either one or both the olefin or hydrogen peroxide is added subsequent to initiation of the process.

Since there is no oxidation of the alcoholic solvent this process is especially suited for a continuous reaction mode in which olefin and hydrogen peroxide are added simultaneously.

Isolation of the resulting epoxide is generally accomplished by fractional distillation to yield the substantially pure epoxide in cases where the epoxide is relatively low boiling.

The following Illustrative Embodiments serve to illustrate the invention only and are not to be taken as limiting the scope of the present invention.

Illustrative Embodiment I

A standard Fisher-Porter glass bottle reactor of approximately 125 ml capacity was charged with the fluoro-alcohol, 50% aqueous hydrogen peroxide, the catalyst and the olefin. Conditions and results are shown in the following Tables 1 and 2.

TABLE 1

The Reaction of Hydrogen Peroxide with Various Olefins

| No. | Olefin | HP[1] ml | % | Catalysts |
|---|---|---|---|---|
| 1 | $C_3$[4] | 8.0 | 50 | $H_2WO_4$ 250mg $Et_3N$ 1.0 ml |
| 2 | $C_3$ | 8.0 | 50 | $H_2WO_4$ 250mg |
| 3 | $C_3$ | 8.0 | 50 | $H_2WO_4$ 250mg, $Et_3NO$ 1.0 ml |
| 4 | $C_3$ | 8.0 | 50[3] | $H_2WO_4$ 250mg, $Et_3NO$ 1.0 ml |
| 5 | $C_2$[4] | 8.0 | 50 | $H_2WO_4$ 250mg, $Et_3NO$ 1.0 ml |
| 6 | Allyl Alcohol 9.5 ml | 8.0 | 50 | $H_2WO_4$ 250mg, $Et_3NO$ 1.0 ml |
| 7 | | | | |
| 8 | Allyl Alcohol 9.5 ml | 8.0 | 50 | $H_2WO_4$ 250mg, $Et_3NO$ 1.0 ml |
| 9 | Allyl Alcohol 9.5 ml | 8.0 | 50 | $H_2WO_4$ 250mg, $Et_3NO$ 1.0 ml |
| 10 | Allyl Alcohol | 8.0 | 50 | $H_2WO_4$ 250mg, $Et_3NO$ 1.0 ml + 2 drops concentrated $H_2SO_4$ |
| 11 | Allyl Chloride 11.4 ml | 8.0 | 50 | $H_2WO_4$ 250mg, $Et_3NO$ 1.0 ml |

| No. | Solvent ml[2] | Time Hrs | Time °C | Results |
|---|---|---|---|---|
| 1 | HFIPA-25 | 6.0 | 60 | 69.9% propylene oxide (PO) |
| 2 | HFIPA-25 | 7.0 | 70 | Exothermic reaction-polymerization of PO |
| 3 | HFIPA-25 | 5.0 | 60 | pH - 2.9 start, 3.9 end; 75 + % PO |
| 4 | HFIPA-15 $H_2O$-10 | 6.0 | 80 | No reaction |
| 5 | HFIPA-25 | 6.5 | 60 | 16% ethylene oxide |
| 6 | PFIPA-25 | 7.5 | 55 | Glycidol |
| 7 | | | | |
| 8 | HFIPA-25 | 5.0 | 60 | ~ 70% yield of glycidol |
| 9 | HFIPA-25 | 5.0 | 50 | 45% yield of glycidol |
| 10 | HFIPA-25 | 6.5 | 125 | IPA forms, no propylene glycol |
| 11 | HFIPA-25 | 6.0 | 60 | ~ 45% epichlorohydrin |

[1]HP - Hydrogen Peroxide
[2]HFIPA - Hexafluoroisopropanol
[3]HP pumped in
[4]$C_3$ = propylene, $C_2$ = ethylene

TABLE 2

The Reaction of Hydrogen Peroxide with Ethylene and Propylene

| No. | Olefin[1] | HP ml | % | Catalysts |
|---|---|---|---|---|
| 12 | $C_2$ | 3 | 50 | $H_2WO_4$ 200 mg |
| 13 | $C_2$ | 3 | 50 | $Na_2WO_4$ 264 mgpH = 9.1 |
| 14 | $C_2$ | 4 | 50 | 1.25 ml[3] |
| 15 | $C_3$ | 4 | 50 | 1 ml[4] |
| 16 | $C_3$ | 4 | 50 | 1 ml[4] |
| 17 | $C_2$ | 4 | 50 | 2 ml[5] |
| 18 | $C_2$ | 4 | 50 | 2 ml[6] |
| 19 | $C_2$ | 4 | 50 | 2 ml[7] |
| 20 | $C_3$ | 4 | 50 | $H_2WO_4$ 125mg, $Et_3NO$ 0.5 ml |
| 21 | $C_3$ | 4 | 50 | $H_2WO_4$ 125mg, $Et_3NO$ 0.5 ml |
| 22 | $C_3$ | 4 | 50 | $H_2WO_4$ 125mg, $Et_3NO$ 0.5 ml |
| 23 | $C_3$ | 4 | 50 | $H_2WO_4$ 125mg, $Et_3NO$ 1.0 ml |

TABLE 2-continued

The Reaction of Hydrogen Peroxide with Ethylene and Propylene

| No. | | | | | Solvent[2] ml | Time Hr | Temp. °C | Results |
|---|---|---|---|---|---|---|---|---|
| 24 | $C_3$ | | 4 | 50 | | | | [8] EtNO 0.5 ml |
| 25 | $C_3$ | | 8 | 50 | | | | $H_2WO_4$ 500 mg, $Et_3NO$ 2.0 ml |
| 26 | $C_3$ | | 4 | 50 | | | | $Re_2O_7$ 242mg, $Et_3NO$ 1.0 ml |
| 27 | $C_3$ | | 8 | 32[9] | | | | $H_2WO_4$ 500 mg, $Et_3NO$ 2.0 ml |
| 28 | $C_3$ | | 4 | 50 | | | | $MoO_2(acac)_2$ 326mg, $Et_3NO$ 1.0 ml |
| 29 | Allyl Chloride 11.4 ml | | 4 | 50 | | | | $H_2WO_4$ 250mg, $Et_3NO$ 1.0 ml |
| 30 | $C_3$ | | 8 | 50 | | | | $H_2WO_4$ 250mg, $Et_3NO$ 1.0 ml |
| 31 | $C_3$ | | 8 | 50 | | | | $H_2WO_4$ 250mg, $Et_3NO$ 1.0 ml |
| 32 | $C_3$ | | 8 | 50 | | | | $H_2WO_4$ 250mg, $Et_3NO$ 1.0 ml |
| 33 | $C_3$ | | 8 | 50 | | | | $H_2WO_4$ 250mg, $Et_3NO$ 1.0 ml |
| 34 | $C_3$ | | 8 | 50 | | | | $H_2WO_4$ 250mg, $Et_3NO$ 1.0 ml |
| 12 | | | | | HFIPA-25 | 2.5 | 55 | Trace 0.5% ethylene oxide |
| 13 | | | | | HFIPA-25 | 5.0 | 56 | No reaction, pH is critical |
| 14 | | | | | HFIPA-25 | 8.0 | 65 | Trace 0.1% ethylene oxide |
| 15 | | | | | HFIPA-25 | 5.0 | 55 | Trace 0.5% ethylene oxide |
| 16 | | | | | HFIPA-25 | 7.0 | 55 | Same propylene oxide 2% |
| 17 | | | | | HFIPA-25 | 7.0 | 55 | Trace ethylene oxide |
| 18 | | | | | HFIPA-25 | 5.0 | 55 | Very slight trace of ethylene oxide |
| 19 | | | | | HFIPA-25 | 5.5 | 55 | No ethylene oxide |
| 20 | | | | | HFIPA-25 | 9.5 | 55 | 50% propylene oxide |
| 21 | | | | | HFIPA-25 | 6.5 | 70 | 70% propylene oxide |
| 22 | | | | | HFIPA-25 | 6.5 | 80 | 60% propylene oxide probably too hot |
| 23 | | | | | HFIPA-25 | 4.5 | 70 | Propylene oxide formed, but reaction died |
| 24 | | | | | HFIPA-25 | 6.5 | 120 | 35% propylene oxide |
| 25 | | | | | HFIPA-25 | 5.0 | 60 | 63% propylene oxide |
| 26 | | | | | HIFPA-25 | 6.0 | 60 | 43.5% propylene oxide |
| 27 | | | | | HFIPA-25 | 5.0 | 60 | 31.8% propylene oxide |
| 28 | | | | | HFIPA-25 | 5.2 | 52 | 47.4% propylene oxide |
| 29 | | | | | HFIPA-25 | 6.0 | 60 | 24.2% epichlorohydrin |
| 30 | | | | | HFIPA-15 TBA-15 | 3.0 | 60 | No reaction |
| 31 | | | | | HFIPA-15 $CH_3CN$-15 | 3.0 | 60 | No reaction |
| 32 | | | | | HFIPA-25 | 4.0 | 80 | $H_2O_2$ decomposes |
| 33 | | | | | Propylene Carbonate-25 | 2.2 | 60 | $H_2O_2$ decomposes |
| 34 | | | | | $CH_3-\overset{O}{\underset{\|}{P}}-(OCH_3)_2$-25 | 1.0 | 35 | Rapid decomposition of $H_2O_2$ |

[1]Initial charge 120 psig $C_2$ = ethylene, $C_3$ = propylene
[2]HFIPA = hexafluoroisopropanol, TBA = tertiary butyl alcohol
[3]4.2 g $Na_2WO_4 \cdot 2H_2O$ in 15 ml $H_2O$ (pH = 9.1) conc. $H_2SO_4$ dropwise till pH = 5.4
[4]4.2 g $Na_2WO_4 \cdot 2H_2O$ in 15 ml $H_2O$ total. Neutralized with $H_3PO_4$ to pH = 7.6
[5]2 ml catalyst solution = 1 mm $WO_4^{-2}$, pH = 4.5 adjusted with 5 $(NH_3)_2SO_4$
[6]2 ml of No. 5 heated to 100° C for 1 hour
[7]Same as No. 5 but pH = 3.4
[8]Propylene glycol molybdate
[9]$H_2O_2$ pumped in.

Illustrative Embodiment II

Illustrative Embodiment I was repeated using isopropyl alcohol (IPA) in place of the hexafluoroisopropyl alcohol (HFIPA) at temperatures ranging from 0°–70° C for periods of time between 3 hours to 2 days. The yield of propylene oxide based on propylene for the IPA case was 0.0% while for the HFIPA case it was as high as 70%.

If in addition to the aqueous hydrogen peroxide a 0.5 to 10 weight percent of acetone is added to the reaction then as much as 23% propylene oxide can be produced.

This illustrates the ineffectiveness of IPA and the enhanced effectiveness of a HFIPA over a IPA/acetone mixture. Furthermore, it explains why some investigators have been incorrectly led to believe that isopropanol was a proper solvent since in every case they made their hydrogen proxide in IPA under conditions which would produce some acetone.

We claim as our invention:

1. In the process for the production of epoxides by contacting an olefin with hydrogen peroxide in an organic solvent in the presence of a transition metal compound and a nitrogen-containing compound the improvement which comprises using as the organic solvent a fluorinated alcohol having the formula:

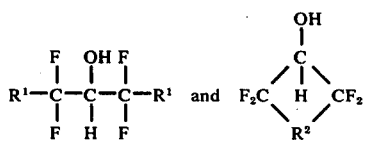

where $R^1$ is a saturated alkyl or fluoroalkyl group having 6 or less carbons, a phenyl group, or a flourine atom and $R^2$ is a saturated alkyl or fluoroalkyl of 2 and 3 carbon atoms which forms part of a 5 or 6 membered ring.

2. The process of claim 1 where the olefin is selected from the group consisting of ethylene, propylene, allyl alcohol and allyl chloride.

3. The process of claim 2 where the olefin is propylene.

4. The process of claim 2 where the olefin is allyl chloride.

5. The process of claim 2 where the transition metal compound is tungstic acid.

6. The process of claim 5 where the fluorinated alcohol is hexafluoroisopropanol.

7. The process of claim 1 where the fluorinated alcohol is selected from the group consisting of hexafluoroisopropanol and perfluoromethyl perfluoroethylcarbinol.

8. The process of claim 7 where the nitrogen-containing compound is a tertiary amine.

9. The process of claim 7 where the nitrogen-containing compound is a tertiary amine oxide.

10. The process of claim 9 where the amine oxide is triethylamine oxide.

* * * * *